United States Patent [19]

Henault et al.

[11] Patent Number: 4,950,237

[45] Date of Patent: Aug. 21, 1990

[54] DUAL CHAMBERED MIXING AND DISPENSING VIAL

[75] Inventors: Paul Henault, Clermont-Ferrand, France; Carleton H. Macartney, Lincroft, N.J.; Gilbert Lataix, Chatel-Guyon, France; Ronald G. Saffron, Salisbury, England

[73] Assignee: Merck & Co., Inc., Rahway, N.J.

[21] Appl. No.: 265,745

[22] Filed: Nov. 1, 1988

[30] Foreign Application Priority Data

Nov. 6, 1987 [GB] United Kingdom ................. 8726062

[51] Int. Cl.[5] .............................................. A61M 37/00

[52] U.S. Cl. .......................................... 604/82; 604/91; 604/416; 222/420; 222/510; 222/215; 222/153; 222/145

[58] Field of Search ........................ 604/82, 86, 88, 89, 604/91, 92, 416, 56; 222/145, 180, 420, 207, 209, 215, 153, 510; 239/304, 323, 328, 331, 407

[56] References Cited

U.S. PATENT DOCUMENTS

| | | | |
|---|---|---|---|
| 2,764,157 | 9/1956 | Oliva et al. | 604/416 |
| 2,764,983 | 10/1956 | Barasch et al. | 604/416 |
| 3,340,878 | 9/1967 | Solowey | 128/272 |
| 3,354,883 | 11/1967 | Southerland | 128/232 |
| 3,397,694 | 8/1968 | Ogle | 128/272 |
| 3,411,503 | 11/1968 | Santomieri | 128/216 |
| 3,464,414 | 9/1969 | Sponnoble | 128/272 |
| 3,809,225 | 5/1974 | Allet-Coche | 604/416 |
| 3,968,872 | 7/1976 | Cavazza | 604/416 |
| 4,315,570 | 2/1982 | Silver et al. | 604/416 |
| 4,330,531 | 5/1982 | Alliger | 424/149 |
| 4,331,146 | 5/1982 | Brignola | 128/218 |
| 4,412,836 | 11/1983 | Brignola | 604/87 |
| 4,467,588 | 7/1984 | Carveth | 604/92 |
| 4,515,586 | 5/1985 | Mendenhall et al. | 604/92 |
| 4,606,734 | 7/1986 | Larkin et al. | 604/88 |
| 4,757,916 | 7/1988 | Goncalves | 604/88 |

FOREIGN PATENT DOCUMENTS

| | | | |
|---|---|---|---|
| 1019500 | 2/1966 | United Kingdom | 604/82 |
| 8726062 | 11/1987 | United Kingdom . | |

*Primary Examiner*—C. Fred Rosenbaum
*Assistant Examiner*—Mark O. Polutta
*Attorney, Agent, or Firm*—William H. Nicholson; Joseph F. DiPrima

[57] ABSTRACT

A dual chambered vial is equipt with a dislodgeable stopper device between the two chambers, whereby components of a mixture may be maintained in separate chambers until comingling is desired. The stopper is dislodged by means of a plunger activated by depression of flexible walls of one chamber.

7 Claims, 3 Drawing Sheets

DUAL CHAMBERED MIXING AND DISPENSING VIAL

BACKGROUND OF THE INVENTION

This invention relates to fluid dispensing devices in which constituents of the fluid mixture can be maintained in separate chambers and in which the separated constituents can be mixed in vitro, when desired, by placing the chambers in communication with one another. A dislodeable stopper serves to maintain separation of mixture components in the two chambers, which can be dislodged by a plunger within one chamber which is activated by the depression of the flexible walls of one of the chambers.

Container devices having multiple compartments for separately enclosed materials to be mixed prior to use are described in U.S. Pat. Nos. 3,340,873, 3,354,883, 3,397,694, 3,411,503, 4,331,146, 4,412,836, and 4,330,531, having a thin diaphragm type membrane separating the two compartments. These systems are not considered entirely reliable because of inability to maintain a fluid-tight seal between the compartments. U.S. Pat. No. 3,464,414 discloses a rigid walled two chambered mixing vial utilizing hydraulic pressure to dislodge a plug member between the two chambers.

SUMMARY OF THE INVENTION

The present invention relates to a dispensing device adapted to hold two substances which are required to be segregated until just prior to dispensation, and to provide a means for in vitro mixing and dispensing of the mixture. Thereby, a mixture having a limited effective life once mixed may be preserved indefinitely by maintaining separate components until use is desired. While one of the constituents must be liquid the other component may be a liquid or a solid.

The dispenser preferably comprises two vertically spaced compartments separated by a valve which can selectively be operated by the user by movement of one compartment towards or away from the other. In use, the dispenser may be presented to a patient with the valve closed to prevent mixing of the two retained substances and to maintain sterility of the constituents. The valve is operated manually by the patient and the dispenser either inverted or shaken to cause the until now separated substances to mix.

The body of the dispenser, which may be provided with a removable cap, can thereafter be squeezed thereby causing droplet, flow or jet of mixed fluid to be emitted from an outlet nozzle of the dispenser. Alternatively, the dispenser includes a septum to permit withdrawal of the mixed substances using a hypodermic needle or the like.

In a preferred construction, the first compartment is positioned above the second compartment, the two being separated by the common wall which includes a seating for a valve; the boundary wall of the second compartment is capable of movement in a direction towards and/or away from the first compartment and the valve includes a valve stem which is engaged by movement of the second compartment to lift the valve away from its seating to enable substances present in the compartments to be mixed.

The second compartment may comprise a flexible structure capable of flexing in the required manner. In a preferred embodiment, the compartment takes the form of a bellows-like member.

Alternatively, the walls of the second compartment comprise a flexiable diaphragm or a plastic bulb capable of returning to its original shape and configuration after movement towards the first compartment.

Accordingly, it is an object of this invention to provide a dual chambered mixing and dispensing vial, operable without the limitations presented in the prior art.

It is another object of this invention to provide a dual chambered mixing and dispensing medicinal vial that is operable by a patient in need of medication comprised of components which must be segregated until use is required.

It is a further object of this invention to provide a dual chambered mixing and dispensing device adaptable to be used with a variety of dispensing means.

Additional objects of this invention will be apparent to persons of ordinary skill in the art upon reading the following detailed description and appended claims and upon reference to the accompanying drawings.

BRIEF DESCRIPTION OF THE DRAWINGS

For a more complete understanding of the invention reference should be made to the embodiment illustrated in greater detail in the accompanying drawings and described below by way of example of the invention.

In the drawings.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

Figure 3:
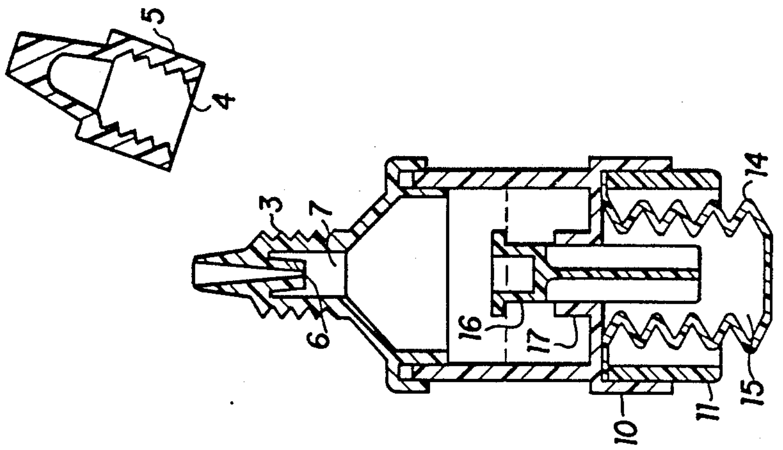
FIG. 3 is a cross-sectional view of the embodiment of FIG. 1 of this invention, being shown after the activation of the stem.
Figure 2:
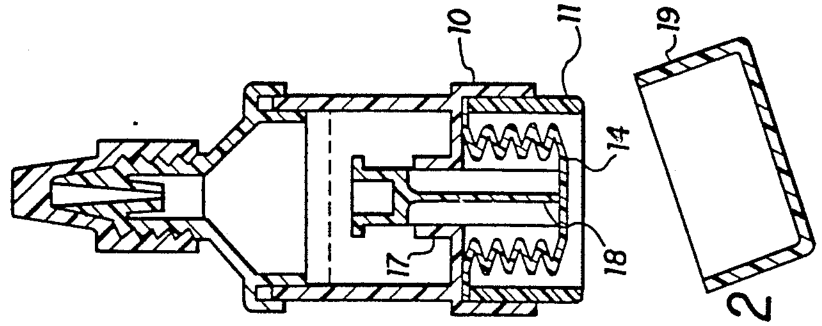
FIG. 2 is a cross sectional view of the embodiment cf FIG. 1 of this invention, being shown with the protective base cap removed and with the stem activated.
Figure 1:
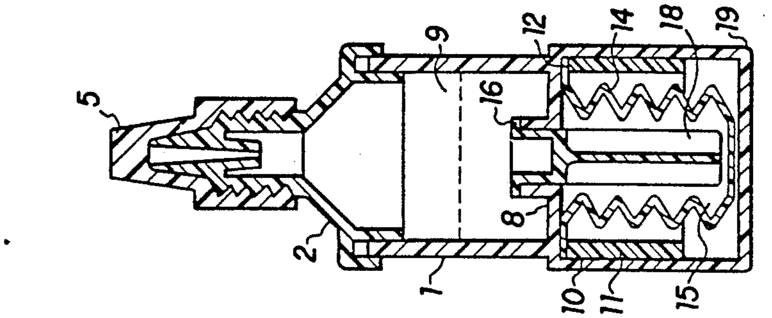
FIG. 1 is a cross-sectional view of the mixing and dispensing device of this invention, being shown prior to the removal of the protective base cup and being shown with a dropper tip dispenser.

As can be seen in Figures 1–3, one embodiment of the mixing and dispensing device of this invention includes a body portion 1 into the upper rim of which is attached nozzle 2. While any suitable means of impermeable attachment may be used, electromagnetic welding is effective for plastic components. The nozzle 2 is provided with external screw threads 3 to receive internal screw threads 4 of a closure cap 5. As illustrated in the embodiment of Figures 1–3 the lower end 6 of the nozzle 2 protrudes downwardly into a generally cylindrical neck 7 for ease of dispensing. It is to be understood, however, that any conventional form of the nozzle may be employed.

The body portion 1, base member 8 and the nozzle 2 essentially define the boundaries of first compartment 9. Protruding downward from base member 8, and parallel to body portion 1 is cylindrical skirt 10. Positioned within and contacting the internal surface of the skirt 10 is ring member 11. Securedly fitted between the upper rim of ring member 11 and the underside of base member 8 is an outwardly extending flange 12 of a vertically flexible bellows 14. This bellows 14, along with the underside of base member 8 defines the second compartment of the mixing and dispensing device. The flange 12 is held in place by a suitable means of attachment, preferably by electro-magnetic welding.

Positioned between the first and second compartments is a valve 16 which fits securedly within a cylindrical collar 17 projecting upward from base member 8 into the first compartment 9 projecting downward from the valve 8 into the second compartment 15 is stem 18. Stem 18 protrudes into the compartment to a position close to or in contact with the bottom of bellows 14.

A rigid, removeable cylindrical base cap 19 closes off the lower portion of the mixing and dispensing vial by fitting onto the ring member 11 up to the point where it meets skirt 10. This base cap may be held in place by any reliable but removeable, securing means, such as push fitting, screw threading, and the like. Tamper proof means, such as a shrink wrap coating may also be used to prevent inadvertant removal of the base cap. Although it is comtemplated that the various components of this dispenser are preferably manufactured from plastic material, any suitable material may be used for one or more of the members.

As illustrated in FIG. 2, when mixture of the components is desired, the base cap 19 is removed, and the bellows 14 is depressed toward the first compartment, thereby raising valve stem 18 and, in turn, dislodging valve 16 from its secured position inside collar 17. Once the valve is dislodged the segregated components can readily mix. This mixture may be facilitated by hydraulic pressure created by the depression and expansion of the bellows 14, or by manually shaking the dispenser. The value stem is designed so that its cross-sectional area is less than the cross sectional area of the orifice formed by collar 17, so that communications can occur between the two compartments even when valve stem 18 is situated within the orifice. An "X" shaped cross-section design of the value stem as can be seen in FIGS. 1-3 has proven effective.

The dispenser may contain in the first compartment a sterile powder, while in the second compartment a sterile diluent. Alternatively, two sterile liquids may be maintained in the separate compartments until mixture is desired.

As illustrated in FIG. 3, once the constituents are mixed, the closure cap 5 may be removed from nozzle 2 to permit dispensing of the mixture as droplets or as liquid streams or jets.

Figure 4:
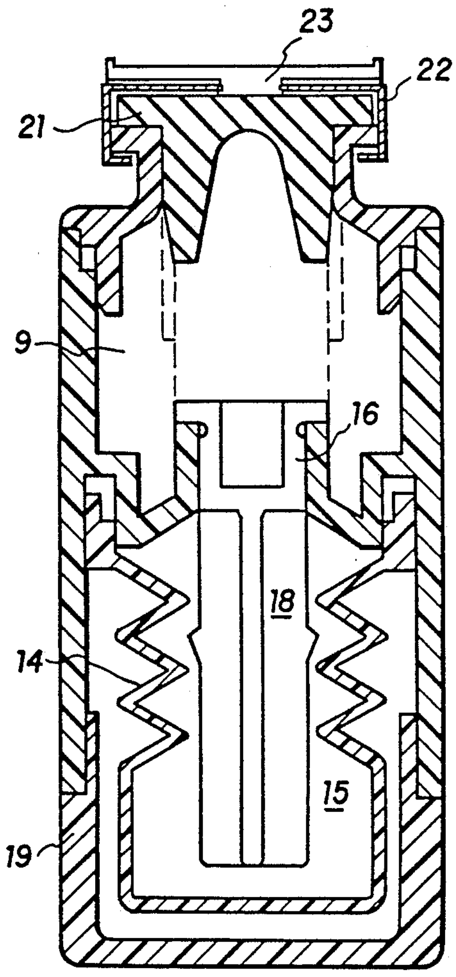
FIG. 4 is a cross-sectional view of the embodiment of FIG. 1 of this invention being shown with a septum dispenser.

FIG. 4 illustrates an alternative embodiment of the mixing and dispensing device of this invention. In this embodiment, ring member 11 has been eliminated, and base cap 19 is designed with inner lip 27 to securedly fit within the lower end of the dispenser wall. Also in this illustration the nozzle dispenser means has been replaced with a stopper 21 produced from a flexible material such as rubber. Until dispensing of the mixture is desired, the upper surface of stopper 21 is secured by an aluminum seal 22 and the dispenser is closed by a removeable cap 23. The seal 22 and rubber stopper 21 define a septum into and through which a hypodermic needle may be inserted to withdraw a dose of the mixture. The mixing operation of the dispensing device illustrated in FIG. 4 is similar to that described in the context of Figures 1-3. However, after mixing and/or dissolving of the components, the cap 23 is removed to expose the upper surface of the aluminum seal 22. A hypodermic needle may then be inserted through the stopper 21, to enable the extraction of a desired dose of the mixture from the dispenser.

Figure 5:
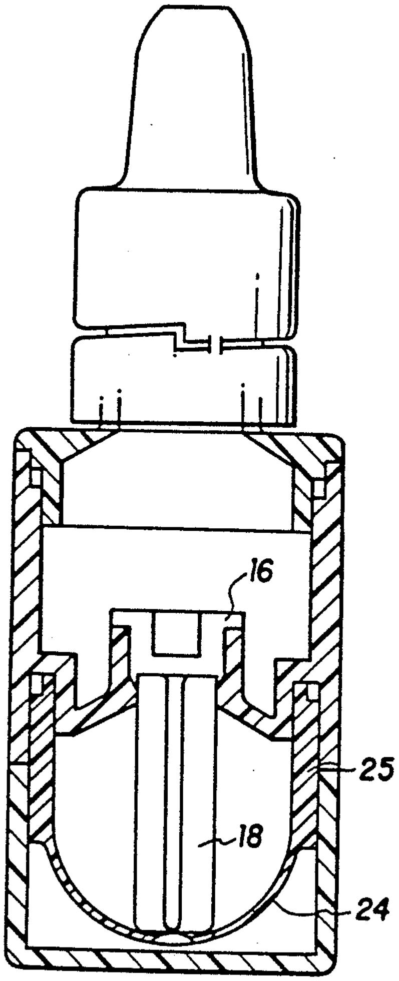
FIG. 5 is a partial cross sectional view of an alternative embodiment of the invention.

In the arrangement illustrated in FIG. 5, the bellows member 14 of the previous illustrations has been replaced with a flexible diaphram 24 dependent from an upper annulus 25. The annulus should be thicker or otherwise substantially non flexible as compared to the flexible diaphram. In other respects the construction and operation of the dispensing device of FIG. 5 is similar to that described above with respect to the embodiment of FIGS. 1-3.

Figure 6:
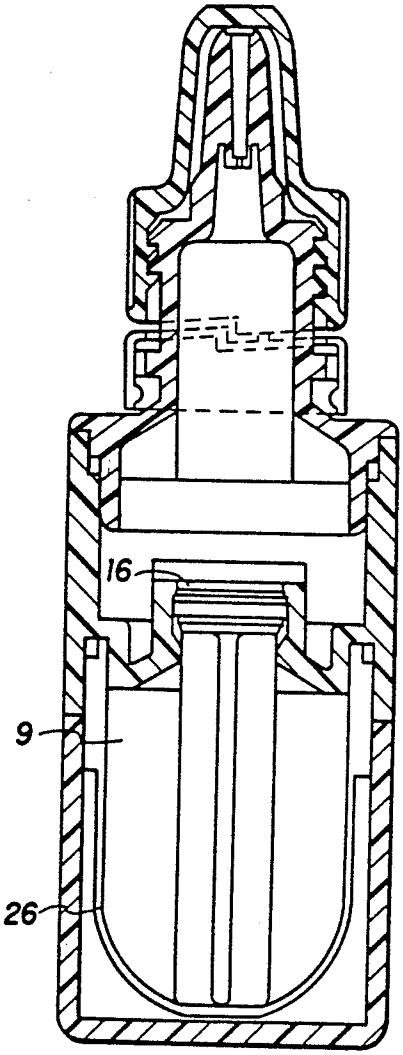
FIG. 6 is a cross sectional view of another alternative embodiment of the invention.

The embodiment of dispensing device illustrated in FIG. 6 is similar to that illustrated in FIG. 5 excepting that, in this embodiment, the lower compartment takes the form of a bulb 26 of plastics material. In this embodiment the dimensions and size of the bulb 26 are such that the bulb returns to its original shape and configuration after initial movement of it towards the upper compartment 9 to operate the valve 16. Thus, in use, and after mixing of the substances contained in the two compartments, the bulb can operate as a dropper mechanism.

It is to be understood that the present invention has been described above purely by way of example and that modifications of detail can readily be made thereto within the scope and spirit of the invention.

Thus, in the embodiment of FIGS. 1 to 3, the member 14 may comprise any construction which facilitates movement of the compartment 15 in a direction towards and/or away from the compartment 9. Thus, compartment 15 may comprise two or more members which can slide one within the other to achieve the required "collapsing" or "expanding" movement.

What is claimed is:

1. A dual chamber mixture dispensing device comprising:

first and second chambers separated from each other by a common wall having an orifice between said two compartments;

a plugging means for selectively sealing said orifice;

a depressible stem situated within said second chamber for dislodging said plugging means from said orifice; and a means for dispensing a mixture from said device comprising a droplet nozzle on said first chamber.

2. The dispensing device of claim 1, wherein the cross-sectional area of the depressible stem is less that the cross-sectional area of said orifice.

3. The dispensing device of claim 1, wherein the walls of the second chamber are selectively depressible toward first chamber to actuate the depressible stem to dislodge the plugging means.

4. The despensing device of claim 3 wherein the walls of the second chamber define a plurality of flexible bellows depressible toward said first chamber.

5. The dispensing device of claim 3, wherein the walls of the second chamber define a flexible bell-shaped base depressible toward said first chamber.

6. The dispensing device of claim 3, further comprising a removeable base cap means securely fitable over said second compartment to prevent non-intentional depression of said walls.

7. A dual chamber mixture dispensing device for selectively maintaining mixture components separate until mixing and dispensing is desired, comprising A. a mixture dispensing means comprising a droplet nozzle;

B. a first chamber carrying the mixture dispensing means for storing one or more of the mixture components, having substantially rigid walls, one of said walls being a common wall to a second chamber, said common wall having an orifice open to said second chamber;

C. a second chamber for storing one or more of the mixture components adjacent to said first chamber extending from said common wall, the other walls and base to said second chamber being selectively depressible toward said first chamber;

D. a plugging means for selectively sealing said orifice having a first position sealing said orifice and a second position dislodged from said orifice; and E. a depressible stem located within said second chamber when said plugging means is in its first position and situated proximately between said plugging means and said flexible base of said second chamber so that depression of said base walls toward the first chamber will cause the depressible flexible stem to dislodge said plugging means from said orifice permitting commingling of the mixture components.

* * * * *